(12) United States Patent
Lodder-Gadaczek et al.

(10) Patent No.: US 12,038,364 B2
(45) Date of Patent: Jul. 16, 2024

(54) MODIFIED FRANZ CELL

(71) Applicant: LTS LOHMANN THERAPIE-SYSTEME AG, Andernach (DE)

(72) Inventors: Julia Lodder-Gadaczek, Selters (DE); Katrin Künzig, Neulussheim (DE); Franziska Frenzel, Neuwied (DE); Tanja Uhrmacher, Daxweiler (DE)

(73) Assignee: LTS Lohmann Therapie-Systeme AG, Andernach (DE)

( * ) Notice: Subject to any disclaimer, the term of this patent is extended or adjusted under 35 U.S.C. 154(b) by 149 days.

(21) Appl. No.: 17/156,016

(22) Filed: Jan. 22, 2021

(65) Prior Publication Data
US 2021/0231547 A1 Jul. 29, 2021

(51) Int. Cl.
*G01N 13/00* (2006.01)
*G01N 1/40* (2006.01)
*G01N 33/15* (2006.01)

(52) U.S. Cl.
CPC ........... *G01N 13/00* (2013.01); *G01N 1/4005* (2013.01); *G01N 33/15* (2013.01); *G01N 2001/4016* (2013.01); *G01N 2013/003* (2013.01)

(58) Field of Classification Search
CPC ...... G01N 13/00; G01N 1/4005; G01N 33/15; G01N 2001/4016; G01N 2013/003
USPC ...................................................... 73/863.23
See application file for complete search history.

(56) References Cited

U.S. PATENT DOCUMENTS

| | | | | |
|---|---|---|---|---|
| 4,594,884 A | * | 6/1986 | Bondi | G01N 13/00 435/287.1 |
| 4,740,309 A | * | 4/1988 | Higuchi | B01D 61/28 210/321.63 |
| 5,198,109 A | * | 3/1993 | Hanson | G01N 13/00 210/321.75 |
| 5,547,351 A | | 8/1996 | Hanua | |

(Continued)

FOREIGN PATENT DOCUMENTS

CN 103217364 A * 7/2013

OTHER PUBLICATIONS

Bram Baert et al., A New Discriminative Criterion for the Development of Franz Diffusion Tests for Transdermal Pharmaceuticals, Jun. 27, 2010, J Pharm Pharmaceut Sci 13(2) 218-230 (Year: 2010).*

(Continued)

*Primary Examiner* — Marrit Eyassu
(74) *Attorney, Agent, or Firm* — Lippes Mathias LLP

(57) ABSTRACT

The present invention relates to an acceptor chamber for a Franz diffusion cell, comprising an upper opening closable by a membrane and, on the side wall of the acceptor chamber, an upper and a lower outlet opening designed to remove or add liquid medium from the acceptor chamber, the upper outlet opening being located within the upper two thirds of the side wall and the lower outlet opening is located in the lower quarter of the side wall, the upper and lower outlet openings being substantially opposite each other, to a Franz diffusion cell comprising a donor compartment and such an acceptor chamber, the donor compartment and the acceptor chamber being separated from each other by a membrane, and to a method for determining the diffusion of a substance through a membrane with such a Franz diffusion cell.

21 Claims, 4 Drawing Sheets

(56) References Cited

U.S. PATENT DOCUMENTS

| | | | | |
|---|---|---|---|---|
| 5,580,365 | A * | 12/1996 | Maiden | C03B 23/207 |
| | | | | 65/153 |
| 10,613,011 | B2 * | 4/2020 | Munt | G01N 13/00 |
| 2003/0180954 | A1 | 9/2003 | Riviere et al. | |
| 2012/0167671 | A1 * | 7/2012 | Mikulasik | B01D 29/48 |
| | | | | 73/61.52 |
| 2012/0324984 | A1 * | 12/2012 | Wakefield | G01N 3/12 |
| | | | | 73/38 |
| 2018/0031465 | A1 * | 2/2018 | Di Cagno | G01N 15/0826 |
| 2018/0259438 | A1 * | 9/2018 | Munt | G01N 13/00 |
| 2019/0022022 | A1 * | 1/2019 | Schobel | A61K 36/61 |
| 2020/0025664 | A1 * | 1/2020 | Mahler | G01N 33/559 |

OTHER PUBLICATIONS

Simon J. Gallagher et al., Effects of Membrane Type and Liquid/Liquid Phase Boundary on In Vitro Release of Ketoprofen from Gel Formulations, 2003, Journal of Drug Targeting, vol. 11 (6), pp. 373-379 (Year: 2003).*

Office Action for German Patent Application 10-2020-101-584.4, dated Sep. 24, 2020, 9 pages.

* cited by examiner

MODIFIED FRANZ CELL

The present application claims the benefit of German Patent Application No. 102020101584.4, filed Jan. 23, 2020. The disclosure of which is herein incorporated by reference.

The present invention relates to an acceptor chamber for a Franz diffusion cell, to a Franz diffusion cell comprising such an acceptor chamber, and to a method for determining the diffusion of a substance through a membrane with such a Franz diffusion cell.

A Franz diffusion cell, or also just Franz cell for short, is an apparatus for testing the active ingredient release of a substance from pharmaceutical dosage forms in vitro in a laboratory.

Such a Franz diffusion cell usually has a donor compartment and an acceptor chamber, which are separated from each other by a membrane. The donor compartment contains the pharmaceutical dosage form comprising the substance to be tested, and the acceptor chamber contains a preferably liquid medium from which samples are taken at defined times in order to determine the diffusion of the substance to be tested through the membrane into the medium.

Franz diffusion cells are known from the prior art.

For example, U.S. Pat. Nos. 5,547,351 and 5,198,109 A1 each disclose a Franz diffusion cell comprising a donor compartment and an acceptor chamber which are separated from each other by a membrane. The side wall of the Franz diffusion cell has an upper and a lower outlet opening placed on the same side of the side wall.

However, such a Franz diffusion cell has disadvantages. Especially with highly lipophilic or poorly soluble active pharmaceutical ingredients, permeation through the membrane into an aqueous acceptor medium cannot be guaranteed. This may lead to false negative results, especially in early feasibility studies. In order to examine permeation of lipophilic or poorly soluble active pharmaceutical ingredients, a suitable lipophilic solvent is layered beneath the aqueous acceptor medium contacting the membrane. This extracts the active pharmaceutical ingredient from the aqueous phase into the organic phase; the concentration in the aqueous fraction is kept very low, and thus the diffusion of lipophilic or poorly soluble active ingredients through the membrane can be analysed.

Such an arrangement of a layer of an organic solvent from beneath is difficult to achieve with the known Franz diffusion cells. The aim of the present invention was therefore to provide an acceptor chamber for a Franz diffusion cell which allows an organic solvent to be layered beneath an aqueous acceptor medium and which also allows samples to be taken from the organic solvent or the organic solvent to be completely exchanged during the diffusion measurement, preferably in such a way that mixing of the solvents is largely avoided. Furthermore, a method is to be provided to determine the diffusion of lipophilic or poorly soluble active pharmaceutical ingredients across a membrane as accurately as possible.

This aim is addressed by an acceptor chamber for a Franz diffusion cell according to claim 1, wherein the acceptor chamber comprises an upper opening closable by a membrane and, on the side wall of the acceptor chamber, an upper and a lower outlet opening designed to remove or add liquid medium from the acceptor chamber, wherein the upper outlet opening is placed within the upper two thirds of the side wall and the lower outlet opening is placed in the lower quarter of the side wall, and characterised in that the upper and lower outlet openings are located substantially opposite each other.

On the one hand, such a design of an acceptor chamber has the advantage that the layering of an organic solvent beneath an aqueous phase and/or a sampling is easily possible through the lower outlet opening. On the other hand, sampling from the organic solvent is easily possible through the lower outlet opening. In addition, the organic solvent can easily be completely exchanged through the lower outlet opening. Furthermore, it is advantageous that the solvent can be easily removed through the lower outlet opening and easily refilled through the upper outlet opening.

Placing the outlet opening on opposite sides of the acceptor chamber has the especial advantage that sampling is much easier and the acceptor chamber or the Franz diffusion cell can be tilted towards the lower outlet opening for sampling without liquid medium escaping from the upper outlet opening.

Furthermore, placing the two outlet openings at different heights according to the present invention has the advantage that aqueous solvent can be removed or organic solvent can be refilled through the upper outlet opening, while samples of the organic solvent can be taken through the lower outlet opening without the two solvents being mixed by the sampling.

The refilling of solvent through the upper outlet opening has the advantage that filling with organic solvent is possible without this coming into contact with the skin/membrane, and thus there is only slight mixing at the phase boundary of aqueous and organic.

In this way, the advantageous properties of a Franz diffusion cell and a separating funnel are combined.

In the following, the term "comprise" can also mean "include" or "consist of".

The terms "outlet" and "inlet", and, respectively, "outlet opening" and "inlet opening" can be used synonymously.

In this description, a distinction is made between Franz diffusion cells and flow diffusion cells. Flow diffusion cells are also called flow-through diffusion cells.

Preferably, the Franz diffusion cell as described herein does not comprise a flow diffusion cell or flow-through diffusion cells.

The expression "substantially opposite each other" is understood to mean that, starting from a perfect arrangement in which the two outlet openings enclose an angle of 180°, the two outlet openings can deviate in both directions by approximately 30°, preferably approximately 20°, especially preferably approximately 10°, and especially approximately 5°.

The term "top" is understood to mean the region of the acceptor chamber that can be closed by the membrane. The term "bottom" is understood to mean the region of the acceptor chamber opposite the opening. Therefore, the lower quarter of the acceptor chamber is understood to be the height as measured from the bottom to one quarter of the height of the chamber from the bottom, and the upper two thirds of the acceptor chamber is understood to be a distance measured starting after one third from the bottom as far as the upper opening.

For example, if the acceptor chamber is 12 cm high, the lower quarter is understood to be the region from 0 to 3 cm measured from the bottom, while the upper two-thirds comprise the region from 4 cm to 12 cm high, measured from the bottom.

The acceptor chamber preferably comprises a hollow body substantially open on one side, the opening being present on the upper side of the hollow body so that this opening is closable by a membrane placed substantially vertically on the opening.

The acceptor chamber according to the invention is preferably characterised in that the upper and/or the lower outlet opening is reclosable. Especially, the lower outlet opening is reclosable. Valves, such as screw valves, or a septum are especially suitable for reclosing. However, it is also possible to close the outlet openings with an adhesive film, such as the "parafilm" commonly used in laboratory work.

Preferably, only the lower outlet opening is closed. The upper outlet opening is preferably designed in such a way that it extends beyond the upper liquid limit and thus no leakage of the liquid is possible, even without closure.

In principle, the acceptor chamber can have any suitable basic shape. Especially preferably, the acceptor chamber has the basic shape of a cylinder, cuboid or cube. Especially preferably, the acceptor chamber has the basic shape of a cylinder. In this case, the cylinder lateral area is the side wall and one of the substantially circular openings is the opening which can be closed by a membrane.

The acceptor chamber according to the invention is preferably characterised in that the lower outlet opening is arranged flush with the bottom of the acceptor chamber. This means that the lower outlet opening is placed in such a way that the acceptor chamber has no or only little dead volume.

The expression "flush with the bottom of the acceptor chamber" is understood to mean that the lower outlet opening is in the range of 0 to 10% of the height of the acceptor chamber, based on the total height of the acceptor chamber, measured from the bottom.

The flush termination of the lower outlet opening with the bottom of the acceptor chamber has the advantage that the organic solvent can be completely removed. By placing the two outlet openings on different sides of the acceptor chamber, the acceptor chamber can be tilted towards the lower outlet opening for complete removal of the organic solvent without aqueous solvent escaping through the upper outlet opening.

The acceptor chamber according to the invention is preferably characterised in that the upper outlet opening is placed within the middle third of the side wall. The middle third is to be understood according to the above definition.

The acceptor chamber according to the invention is preferably characterised in that the upper outlet opening is placed within the upper third of the side wall. The upper third is to be understood according to the above definition.

The acceptor chamber according to the invention is preferably characterised in that the acceptor chamber has a volume of 2 ml to 50 ml, preferably of 5 ml to 20 ml. Especially, the acceptor chamber has a volume of 8 ml to 12 ml, very especially preferably 9.5 ml.

The acceptor chamber according to the invention is preferably characterised in that it has a height of approximately from 4 to 15, preferably from 5 to 14, and a base area of from 1 cm 2 to 4 cm 2, preferably from 1.77 cm 2 to 4 cm 2.

The acceptor chamber according to the invention is preferably characterised in that it is constructed from a transparent material. Suitable materials comprise borosilicate glass and also plastics.

The acceptor chamber according to the invention is preferably characterised in that the upper and/or the lower outlet opening are inclined at an angle of from approximately 30° to approximately 80° in the direction of the opening which can be closed by a membrane.

The lower outlet opening should preferably be adapted to the closure device used, preferably a valve. Preferably, the lower outlet opening comprises a U-piece to the closure device, preferably to the valve, and then an outlet inclined downwards at an angle of from 30 to 60°, preferably of approximately 45°.

The acceptor chamber according to the invention is preferably characterised in that the lower outlet opening is first inclined upwards at an angle of from 60° to 80° and then inclined downwards at an angle of from 30° to 60°, preferably of approximately 45°.

The acceptor chamber according to the invention is preferably characterised in that the upper and/or the lower outlet opening are shaped in such a way that they initially run parallel to the base area and then bend at an angle of from approximately 30 to approximately 90° in the direction of the openings which can be closed by a membrane.

Mixed forms of the two above embodiments are also possible.

The present invention further comprises a Franz diffusion cell comprising a donor compartment and an acceptor chamber as described above, wherein the donor compartment and the acceptor chamber are separated by a membrane.

The donor compartment does not necessarily have to be a chamber or a closed room that is filled with the substance to be tested.

Preferably, the donor compartment comprises the substance to be tested or a pharmaceutical dosage form comprising the substance to be tested. Preferably, the substance to be tested or a pharmaceutical dosage form comprising the substance to be tested is applied as a donor compartment to the membrane and the free space around the membrane or around the substance to be tested or around the pharmaceutical dosage form comprising the substance to be tested is closed by a closure so that no external influences can act on the membrane or the substance to be tested or on the pharmaceutical dosage form comprising the substance to be tested.

Especially preferably, the membrane comprises human or animal skin and/or a synthetic membrane.

The Franz diffusion cell according to the invention further preferably comprises means for maintaining the temperature of the solvents in the acceptor chamber at a constant value of preferably from 25 to 40° C., more preferably from 32 to 37° C.

Alternatively, the Franz diffusion cell can also be placed in an incubator to maintain a constant value of preferably from 25 to 40° C., more preferably 32 to 37° C.

The present invention also relates to a method for determining the diffusion of a substance through a membrane using a Franz diffusion cell as described above. This method comprises the steps of:

filling the acceptor chamber with an aqueous solvent and an organic solvent immiscible with the aqueous solvent, wherein the organic solvent has a higher density than the aqueous solvent and the amounts of the aqueous and the organic solvent are chosen such that the entire acceptor chamber is filled so that the liquid contacts the underside of the membrane, and wherein the phase boundary of the two immiscible solvents lies between the upper and the lower outlet opening, and applying the donor compartment, comprising the substance to be tested, to the membrane.

If the Franz diffusion cell is filled with the two different solvents in such a way that the phase boundary lies between the upper and the lower outlet opening, this has the advantage that samples can be easily taken from the respective solvents without the two solvents being mixed. Especially, it is possible that samples of the organic solvent can be taken through the lower outlet opening or that the organic solvent can be completely exchanged.

The method is advantageous for measuring the permeation of highly lipophilic or poorly soluble substances for which no sinking conditions can be maintained in a conventional permeation with an aqueous acceptor due to the very poor solubility of the active ingredient. The use of a two-phase system with a lower organic, preferably very lipophilic layer, ensures that there is a continuous removal of the active ingredient from the aqueous phase into the organic fraction and thus constant sinking conditions can be maintained in the aqueous fraction. This corresponds in part to the process of a flow-through cell known from the prior art (in which the concentrations are often too low to be measurable), but in a static arrangement. In the organic fraction, the permeated amount of active ingredient can be precisely quantified. The acceptor exchange preferably only takes place in the organic fraction.

Preferably, the aqueous fraction is also removed at the end of the measurement to determine the total balance.

Preferably, the aqueous solvent comprises an aqueous buffer solution in which a preferably physiological pH of preferably from 5.5 to 7.4 is set.

The organic solvent comprises a solvent having a density greater than the density of the aqueous solvent. The organic solvent preferably comprises chloroform.

Preferably, 6.5 ml of the aqueous solvent and 3 ml of the organic solvent, preferably chloroform, are used. It is clear to a person skilled in the art that the Franz diffusion cell must be dimensioned so that the volume of the Franz diffusion cell is approximately 10 ml.

The method according to the invention is preferably characterised in that the donor compartment comprises a transdermal patch, cream, gel, lotion and/or ointment containing the substance to be tested. This means that the transdermal patch, cream, gel, lotion and/or ointment containing the substance to be tested is/are applied directly to the upper side.

Liquids can also be tested by applying impregnated fleeces.

A transdermal patch (also called a transdermal therapeutic system) is understood to mean a system to be applied to the skin, preferably a patch, with a defined application surface, which can deliver a pharmaceutically active ingredient to a patient's body in a controlled manner, preferably according to time and quantity.

Such systems usually have a backing layer that protects the patch and its contents from the outside and may be printed with information. Towards the skin side, the patch is preferably provided with a release liner that covers the sticky side of the system. The release liner is removed before the system is applied and is often siliconised to facilitate removal.

With regard to the technique of controlled drug delivery from the system, a distinction can be made between matrix systems (matrix patches) and membrane systems (also called reservoir or depot systems or reservoir or depot patches).

In matrix systems, the active ingredient is contained in a matrix consisting of one or more layers, which is applied directly to the skin with the aid of an adhesive layer. Embodiments are also possible in which the matrix is also the adhesive layer. The diffusion rate of the active ingredient out of the matrix determines the resorption rate. In some embodiments, there may be an additional membrane between the matrix and adhesive layers that controls the flow of active ingredient.

In the membrane systems, a reservoir of the active ingredient lies under a carrier film, which is released from the reservoir through a porous membrane into the skin in a controlled manner.

The advantages of a transdermal therapeutic system on the patient side are a safe, reliable, exact and painless dosage of pharmaceutically active ingredients and easier therapy or handling for children, elderly patients and patients in need of care. Furthermore, transdermal therapeutic systems are ideal for patients with swallowing difficulties and for extended dosing intervals, especially with multi-day patches.

The advantages of a transdermal therapeutic system on the manufacturer's side are the possible formulation of pharmaceutically active ingredients with only low oral bioavailability, a controlled, uniform delivery of pharmaceutically active ingredients without active ingredient peaks, a good possibility to control the drug dosage by varying the area, no loss of active ingredient by avoiding first-pass metabolism in the liver and no breakdown of the active ingredient in the gastrointestinal tract.

Gels usually comprise gelled liquids. They are preferably produced with suitable swelling agents (gelling agents). These include, for example, celluloses, starches, carbomers, gelatine, xanthan, bentonite, agar and/or pectin.

A distinction is made between hydrophilic and lipophilic gels. Gels can be transparent or opaque.

Other possible ingredients include water, propylene glycol, antioxidants, lipids (in lipogels), flavourings, sweeteners and/or preservatives.

Among other things, gels are used for the local or systemic administration of active ingredients and for moist wound treatment.

A lotion is an externally applied liquid aqueous or aqueous-alcoholic preparation containing suspended or emulsified pharmaceutically active ingredients, and possibly excipients.

Lotions are usually more liquid than creams or ointments and are therefore easier to apply to large areas of the skin.

A lotion is an oil-in-water emulsion or water-in-oil emulsion that is applied externally. It is very light and does not lubricate.

Lotions are used, among other things, for the local or systemic administration of active ingredients and for moist wound treatment.

An ointment, preferably a suspension ointment, is a semi-solid preparation for external use. Ointments preferably consist of a single-phase base in which solid or liquid substances may be dispersed.

A distinction is made between hydrophobic ointments, water-absorbing ointments and hydrophilic ointments. Ointments can also contain emulsifiers and water.

For example, fatty oils, fats, waxes, petroleum products such as petroleum jelly and paraffins, triglycerides and/or macrogols (PEG) can be used to produce ointments.

Ointments are used, among other things, for the local or systemic administration of active ingredients and for moist wound treatment.

A cream is a semi-solid preparation, usually for application to the skin.

A cream is preferably a multi-phase preparation consisting of a lipophilic and an aqueous phase and containing at least one pharmaceutically active ingredient. A distinction is made between a hydrophilic cream (oil-in-water) and a lipophilic/hydrophobic cream (water-in-oil).

A cream is used, among other things, for the local or systemic administration of active ingredients and for moist wound treatment.

Preferably, the donor compartment comprises a transdermal patch containing the substance to be tested, preferably an active pharmaceutical ingredient.

The method according to the invention is preferably characterised in that the substance to be tested comprises a lipophilic active pharmaceutical ingredient, preferably with a log P>1, preferably with a log P>1.5, especially preferably with a log P>2.

The n-octanol-water partition coefficient $K_{ow}$ (spellings such as octanol/water partition coefficient are also common and correct) is a dimensionless partition coefficient known to a person skilled in the art which indicates the ratio of the concentrations of a chemical in a two-phase system of n-octanol and water and is thus a measure of the hydrophobicity or hydrophilicity of a substance. The logP value is the decadic logarithm of the n-octanol-water partition coefficient $K_{ow}$. The following applies:

$$K_{ow} = P = \frac{c_0^{Si}}{c_w^{Si}} \text{ and } \log P = \log\frac{c_0^{Si}}{c_w^{Si}} = \log_{coSi} - c_w^{Si}$$

where $c_o^{Si}$=concentration of a chemical in the octanol-rich phase and $c_w^{Si}$=concentration of a chemical in the water-rich phase.

$K_{ow}$ is greater than one if a substance is more soluble in fat-like solvents such as n-octanol, and less than one if it is more soluble in water. Accordingly, log P is positive for lipophilic and negative for hydrophilic substances.

The method according to the invention is preferably characterised by the fact that, when filling the Franz diffusion cell, the aqueous solvent is introduced and then, through the lower outlet opening, a layer of the organic solvent is arranged beneath. This has the advantage that the acceptor chamber can be filled in two phases without mixing the two liquids.

The method according to the invention is preferably characterised in that, during the first filling, organic solvent and then aqueous solvent are first added. Subsequently, preferably only organic solvent is removed and refilled.

The method according to the invention is preferably characterised in that, during the method, samples of the organic solvent are taken through the lower outlet opening and/or the organic solvent is completely exchanged at least once through the lower and/or the upper outlet opening.

Preferably, the organic solvent is removed through the lower outlet opening and refilled again through the upper outlet opening.

Especially, the advantage of placing the outlet openings on different sides is that the lower outlet opening is easily accessible and (almost) complete removal of the organic solvent is possible.

The method according to the invention is preferably characterised in that the Franz diffusion cell is tilted in the direction of the lower outlet opening for sampling or for complete exchange of the organic solvent.

Placing the outlet openings on different sides has the advantage that no medium escapes through the upper outlet opening when the Franz diffusion cell is tilted towards the lower outlet opening.

Figure 1:
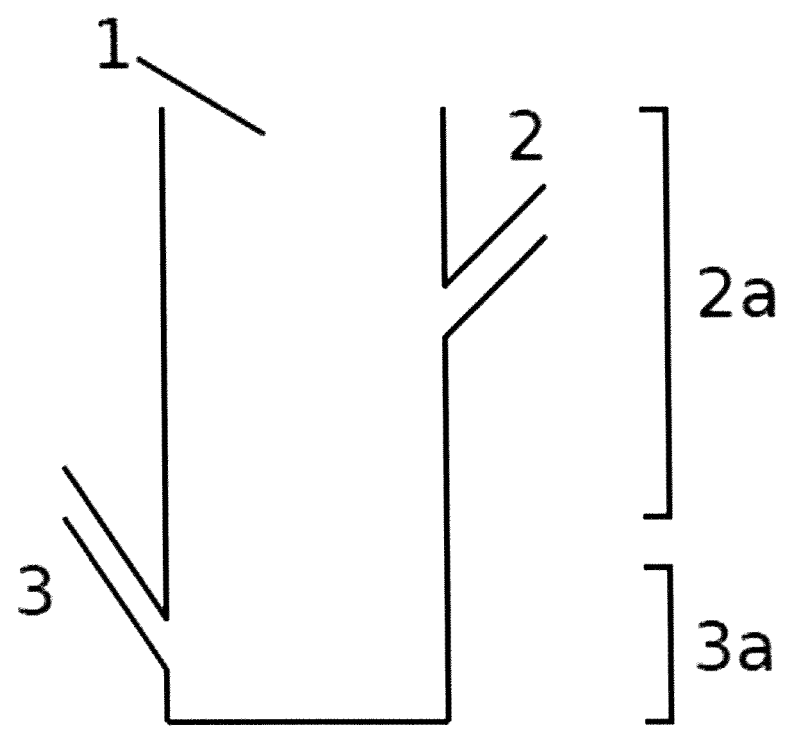
FIG. 1:
Preferred embodiment of the acceptor chamber for a Franz diffusion cell according to the invention, comprising an upper opening (1) closable by a membrane and, on the side wall of the acceptor chamber, an upper (2) and a lower (3) outlet opening designed to remove or add liquid medium from the acceptor chamber, the upper outlet opening being placed within the upper two-thirds (2a) of the side wall and the lower outlet opening being placed in the lower quarter (3a) of the side wall, the upper and lower outlet openings being substantially opposite each other.
Figure 2:
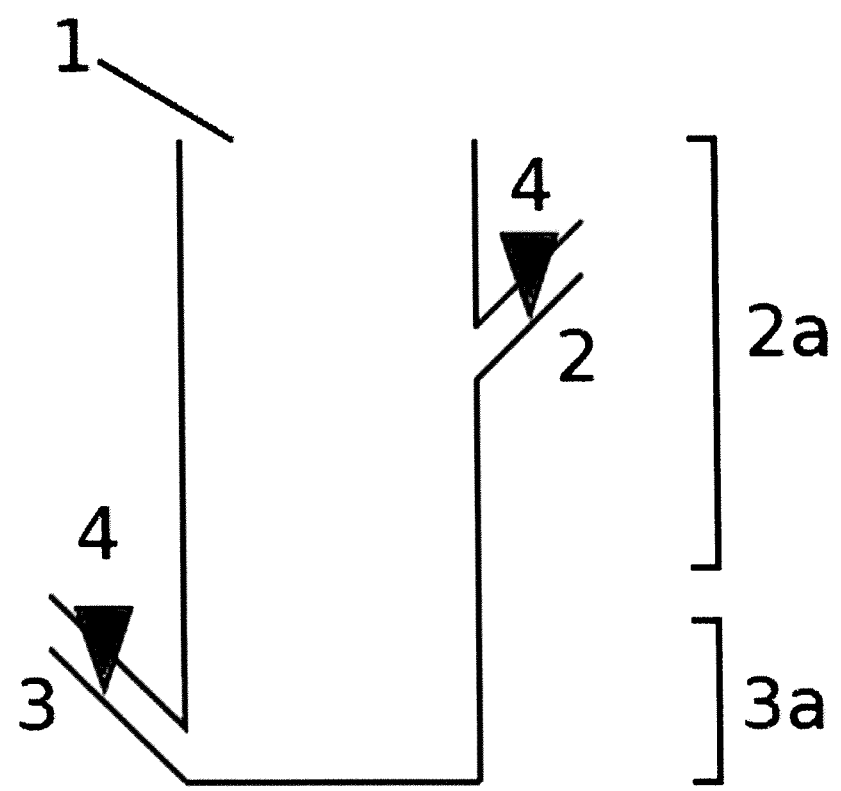
FIG. 2:
Preferred embodiment of the acceptor chamber for a Franz diffusion cell according to the invention, comprising an upper opening (1) closable by a membrane and, on the side wall of the acceptor chamber, an upper (2) and a lower (3) outlet opening designed to remove or add liquid medium from the acceptor chamber, wherein the upper outlet opening is placed within the upper two thirds (2a) of the side wall and the lower outlet opening is placed in the lower quarter (3a) of the side wall so as to terminate flush with the bottom and the two outlet openings are reclosable by a valve (4), the upper and lower outlet openings being substantially opposite each other.
Figure 3:
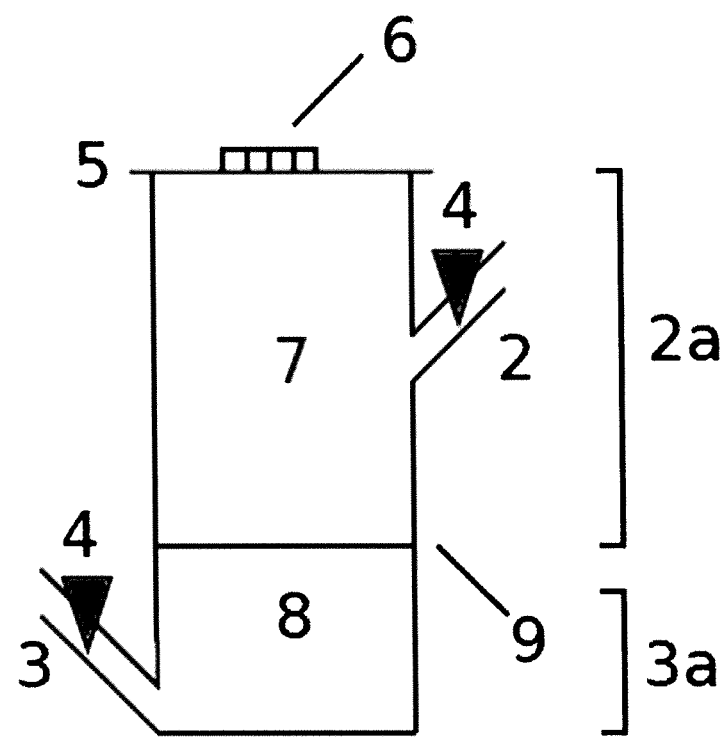
FIG. 3:
Preferred embodiment of a Franz diffusion cell comprising a donor compartment (6) and an acceptor chamber, wherein the donor compartment and the acceptor chamber are separated from each other by a membrane (5). The acceptor chamber comprises an upper opening (1) closable by a membrane and, on the side wall of the acceptor chamber, an upper (2) and a lower (3) outlet opening designed to remove or add liquid medium from the acceptor chamber, the upper outlet opening being placed within the upper two thirds (2a) of the side wall and the lower outlet opening being placed in the lower quarter (3a) of the side wall so as to terminate flush with the bottom and the two outlet openings being reclosable by a valve (4), the upper and lower outlet openings being located substantially opposite each other. The acceptor chamber is filled with an aqueous solvent (7), with a layer of an organic solvent (8) being arranged beneath. The phase boundary (9) is located between the upper (2) and the lower (3) outlet opening.
Figure 4:
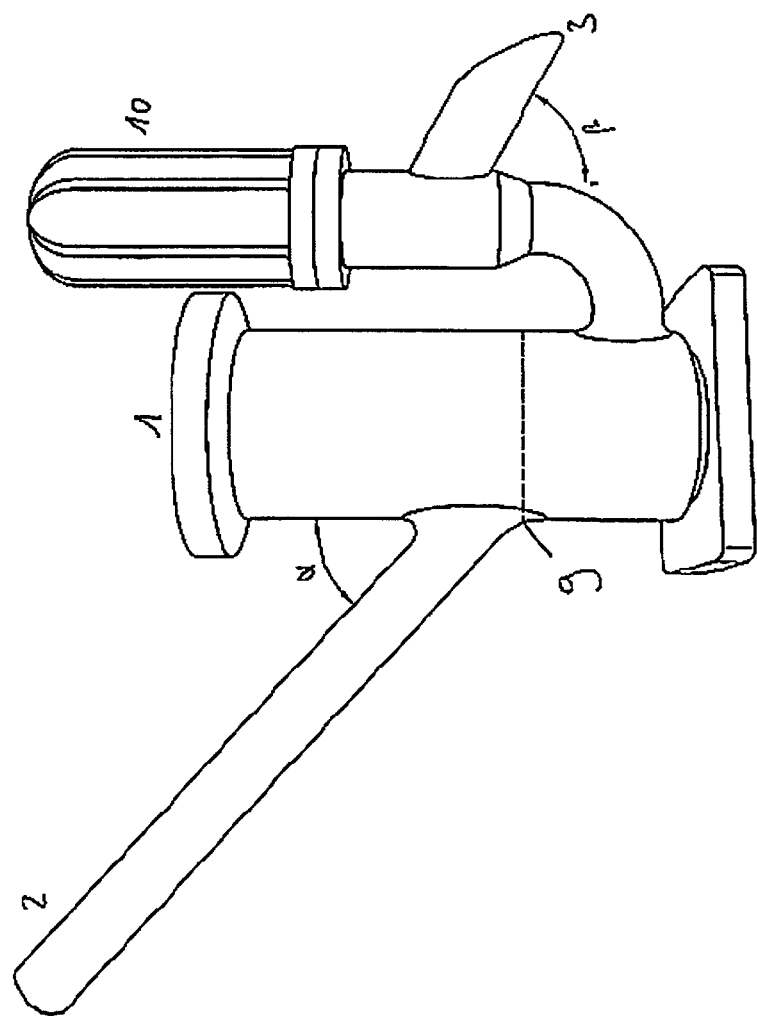
FIG. 4:
Schematic drawing of a preferred embodiment of the acceptor chamber according to the invention.
(2) Upper outlet opening (inlet)
(3) Lower outlet opening with capillary for precise removal
(9) Organic phase fill level
(10) Rotary valve
(α) 45° angle
(β) 60° angle

The invention claimed is:
1. An acceptor chamber for a Franz diffusion cell, comprising an upper opening closable by a membrane and, on a side wall of the acceptor chamber, an upper and a lower outlet opening designed to remove or add liquid medium, and wherein an organic solvent is layered beneath aqueous acceptor medium, from the acceptor chamber, wherein the upper outlet opening is placed within an upper two thirds of the side wall and the lower outlet opening is placed in a lower quarter of the side wall, characterised in that the upper and lower outlet openings are located substantially opposite side from each other, and wherein starting from a perfect arrangement in which the two outlet openings enclose an angle of 180°, the two outlet openings deviate in both directions by up to 30°.

2. The acceptor chamber according to claim 1, characterised in that the upper and/or the lower outlet opening is reclosable.

3. The acceptor chamber according to claim 1, characterised in that the acceptor chamber has a basic shape of a cylinder, cuboid or cube.

4. The acceptor chamber according to claim 1, characterised in that the lower outlet opening is arranged flush with the bottom of the acceptor chamber.

5. The acceptor chamber according to claim 4, characterized in that the lower outlet opening comprises an elbow extending upwardly from the side wall and includes a downwardly depending leg extending from the elbow.

6. The acceptor chamber according to claim 5, characterized in that the upper outlet opening extends upwardly from the side wall.

7. The acceptor chamber according to claim 6, characterized in that the upper outlet opening extends upwardly at an angle relative to vertical less than an angle relative to vertical at which the downwardly depending leg extends.

8. The acceptor chamber according to claim 1, characterised in that the upper outlet opening is placed within an upper third of the side wall.

9. The acceptor chamber according to claim 1, characterized in that the acceptor chamber has a volume of from 2 ml to 50 ml.

10. The acceptor chamber according to claim 1, characterised in that the acceptor chamber is made of borosilicate glass.

11. The acceptor chamber according to claim 1, characterized in that the acceptor chamber has a volume of from 5 ml to 20 ml.

12. The acceptor chamber according to claim 1, characterized in that the lower outlet opening comprises an elbow extending upwardly from the side wall and includes a downwardly depending leg extending from the elbow.

13. The acceptor chamber according to claim 1, characterized in that the upper and lower outlet openings are located opposite each other, wherein the upper and lower outlet openings are each configured to remove or add liquid medium from the acceptor chamber, and wherein samples taken from the organic solvent are completely exchanged during a diffusion measurement.

14. A Franz diffusion cell comprising a donor compartment and an acceptor chamber, comprising an upper opening closable by a membrane and, on a side wall of the acceptor chamber, an upper and a lower outlet opening designed to remove or add liquid medium from the acceptor chamber, wherein the upper outlet opening is placed within an upper two thirds of the side wall and the lower outlet opening is placed in a lower quarter of the side wall, characterised in that the upper and lower outlet openings are located substantially opposite side from each other, wherein the donor compartment and the acceptor chamber are separated from each other by the membrane, and wherein starting from a perfect arrangement in which the two outlet openings enclose an angle of 180°, the two outlet openings deviate in both directions by up to 30°.

15. The Franz diffusion cell according to claim 14, characterised in that the membrane comprises human or animal skin and/or a synthetic membrane.

16. A method for determining the diffusion of a substance through a membrane with a Franz diffusion cell according to claim 14 comprising the steps of:
    filling the acceptor chamber with an aqueous solvent and an organic solvent immiscible with the aqueous solvent, wherein the organic solvent has a higher density than the aqueous solvent and the amounts of the aqueous and the organic solvents are chosen so that the entire acceptor chamber is filled so that the liquid contacts the underside of the membrane, and wherein a phase boundary of the two immiscible solvents lies between the upper and lower outlet openings, and
    applying the donor compartment comprising the substance to be tested to the membrane.

17. The method according to claim 16, characterised in that the donor compartment comprises a transdermal patch, cream, gel, lotion and/or ointment containing the substance to be tested.

18. The method according to claim 16, characterised in that the substance to be tested comprises a lipophilic active pharmaceutical ingredient with a log P>1.

19. The method according to claim 16, characterised in that, when filling the Franz diffusion cell, the aqueous solvent is introduced and then, through the lower outlet opening, a layer of the organic solvent is arranged beneath.

20. The method according to claim 16, characterised in that, during the method, samples of the organic solvent are taken through the lower outlet opening and/or the organic solvent is completely exchanged at least once through the lower outlet opening.

21. The method according to claim 16, characterised in that, for sampling or for complete exchange of the organic solvent, the Franz diffusion cell is tilted towards the lower outlet opening.

* * * * *